(12) United States Patent
Nakamura et al.

(10) Patent No.: US 6,303,383 B1
(45) Date of Patent: Oct. 16, 2001

(54) TEMPERATURE SENSITIVE PLASMID FOR CORYNEFORM BACTERIA

(75) Inventors: Jun Nakamura; Sohei Kanno; Eiichiro Kimura; Kazuhiko Matsui; Tsuyoshi Nakamatsu, all of Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/521,668

(22) Filed: Mar. 8, 2000

(30) Foreign Application Priority Data

Mar. 16, 1999 (JP) .................................................. 11-069896

(51) Int. Cl.[7] .............................. C12N 15/74; C12N 1/20; C12N 15/00; C12N 15/77; C07H 21/04
(52) U.S. Cl. ................. 435/477; 435/252.32; 435/320.1; 536/23.1; 536/23.7
(58) Field of Search ................................ 435/320.1, 477, 435/252.32; 536/23.1, 23.7

(56) References Cited

U.S. PATENT DOCUMENTS

| | | | |
|---|---|---|---|
| 4,778,762 | 10/1988 | Miwa et al. | 435/320 |
| 4,954,441 | * 9/1990 | Katsumata et al. | 435/115 |
| 5,616,480 | 4/1997 | Sugimoto et al. | 435/172.3 |
| 5,756,347 | 5/1998 | Sugimoto et al. | 435/320.1 |

FOREIGN PATENT DOCUMENTS 0 093 611    11/1983   (EP) .

OTHER PUBLICATIONS

S. Ankri, et al., Medline, 12 pages, "Electrotransformation of Highly DNA–Restrictive Corynebacteria with Synthetic DNA", Jan. 22, 1999.

Miwa et al. Gene 39:281–286, 1985.*

Morinaga et al. Agric. Biol. Chem. 51:93–100, 1987.*

* cited by examiner

*Primary Examiner*—James Ketter
*Assistant Examiner*—Lisa Gansheroff
(74) *Attorney, Agent, or Firm*—Oblon, Spivak, McClelland, Maier & Neustadt, P.C.

(57) ABSTRACT

A coryneform bacterium in which a DNA fragment is incorporated into its chromosome is prepared by (a) obtaining a recombinant plasmid through ligation of a DNA fragment having a sequence homologous to a gene present on a chromosome of a coryneform bacterium to a plasmid that has a wild-type replication control region segment of a particular nucleotide sequence including a mutation and is autonomously replicable in a coryneform bacterium cell at a culture temperature lower than 31° C. but not autonomously replicable in the cell at a temperature of 31° C. or higher, (b) introducing the recombinant plasmid into the coryneform bacterium cell, (c) culturing the bacterium at a temperature of 31° C. or higher, (d) causing homologous recombination between the DNA fragment and the gene present on the chromosome of the coryneform bacterium and having a sequence homologous to the DNA fragment, and (e) selecting a coryneform bacterium in which the DNA fragment is incorporated into its chromosome. According to the present invention, there is provided a method for efficiently modifying genetic traits of a host in a short period of time by obtaining a temperature sensitive plasmid from a plasmid not exhibiting homology with already reported temperature sensitive plasmids or not exhibiting incompatibility therewith.

13 Claims, 2 Drawing Sheets

TEMPERATURE SENSITIVE PLASMID FOR CORYNEFORM BACTERIA

BACKGROUND OF THE INVENTION

1. Field of the Invention

The present invention relates to a novel temperature sensitive plasmid for coryneform bacteria. This plasmid can be utilized for modifying a chromosomal gene of coryneform bacteria, which are used for the production of useful substances such as amino acids by fermentation, to change their genetic traits. Thus, the plasmid can be utilized for breeding of microorganisms useful for the production of amino acids by fermentation and so forth.

2. Related Art

There has already been reported an attempt to alter a genetic trait of coryneform bacteria by intentionally modifying a particular gene on their chromosomes, or by stably incorporating a gene of a defined copy number into the chromosomes, thereby utilizing such coryneform bacteria for the production of useful substances such as amino acids by fermentation [Japanese Patent Publication Laid-open (Kokai) No. 5-7491]. This utilizes a plasmid in which a replication control region of the plasmid DNA enabling autonomous replication of the plasmid is modified to be a replication control region having temperature sensitive mutation, which makes the replication impossible when the culture temperature is elevated. However, when such a plasmid containing a temperature sensitive replication control region is used in coryneform bacteria harboring another plasmid having a wild-type replication control region from which the temperature sensitive replication control region has been derived, homologous recombination may be caused between the plasmids. Thus, a phenomenon that the plasmid harbored by the transformant no longer has the temperature sensitive replication control region has been observed. Similarly, when it is intended to modify a gene on a chromosome of coryneform bacteria using such a plasmid, a phenomenon that this plasmid is eliminated due to incompatibility in the process of breeding has also been observed if a host coryneform bacterium harbors a plasmid which has a replication control region of the same origin as the aforementioned plasmid.

SUMMARY OF THE INVENTION

An object of the present invention is to obtain a temperature sensitive plasmid not exhibiting homology with already reported temperature sensitive plasmids or not exhibiting incompatibility therewith, thereby providing a method for efficiently modifying genetic traits of a host in a short period of time.

The inventors of the present invention actively studied in order to achieve the aforementioned object. As a result, they successfully obtained a plasmid containing a mutation that permitted its autonomous replication at a low temperature but did not permit its autonomous replication at an elevated temperature from a plasmid pAM330 extracted from *Brevibacterium lactofermentum* ATCC13869 [Japanese Patent Publication Laid-open (Kokai) No. 58-67699; Miwa, K. et al., Agric. Biol. Chem., 48, 2901 (1984)]. Thus, they accomplished the present invention.

That is, the present invention provides a plasmid containing a temperature sensitive replication control region and a marker gene, wherein the sensitive replication control region is derived from a plasmid pAM330 harbored by *Brevibacterium lactofermentum* ATCC13869 and allows the plasmid to replicate autonomously at a low temperature but does not allow the plasmid to replicate autonomously at an elevated temperature in coryneform bacteria within a temperature range in which the bacteria can grow.

The aforementioned marker gene is preferably an antibiotic resistance gene derived from a bacterium belonging to the genus Streptococcus, and specific examples thereof include a kanamycin resistance gene, tetracycline resistance gene, spectinomycin resistance and so forth.

In a preferred embodiment of the aforementioned plasmid, the plasmid further contains a replication control region that enables autonomous replication of the plasmid in Escherichia bacteria.

The present invention also provides a temperature sensitive replication control region, which is a replication control region included in the nucleotide sequence of SEQ ID NO: 17 and derived from a plasmid pAM330 harbored by *Brevibacterium lactofermentum* ATCC13869, contains one or more mutations selected from a mutation for substitution of T for C at the nucleotide number 1255, mutation for substitution of T for C at the nucleotide number 1534, mutation for substitution of A for G at the nucleotide number 1866, mutation for substitution of A for G at the nucleotide number 2058, mutation for substitution of T for C at the nucleotide number 2187, and mutation for substitution of A for G at the nucleotide number 3193 in the nucleotide sequence, and allows autonomous replication at a low temperature but does not allow autonomous replication at an elevated temperature within a temperature range in which coryneform bacteria can grow.

The present invention further provides a method for creating a coryneform bacterium in which a DNA fragment is incorporated into its chromosome, which comprises the following steps of:

(a) introducing a recombinant plasmid obtained by ligating a DNA fragment having a sequence homologous to a DNA sequence present on a chromosome of a coryneform bacterium to the aforementioned plasmid into a coryneform bacterium cell, (b) culturing the bacterium at a temperature at which the plasmid is autonomously replicable to cause homologous recombination between the DNA fragment and the DNA sequence having a sequence homologous to the DNA fragment present on the chromosome of the coryneform bacterium, and (c) selecting a bacterium in which the DNA fragment is incorporated into the chromosome together with the plasmid.

In a preferred embodiment of the aforementioned method, the method further comprises the following steps of:

(d) culturing the bacterium to cause homologous recombination between the DNA fragment incorporated into the chromosome and a DNA sequence which has a sequence homologous to the DNA fragment and originally exists on the chromosome of the coryneform bacterium, (e) culturing the bacterium at an elevated temperature to eliminate the DNA sequence which originally exists on the chromosome and the plasmid from the chromosome, and (f) selecting a bacterium in which the DNA sequence on the chromosome is replaced with the DNA fragment.

The term "temperature sensitive replication control region" used for the present invention refers to a replication control region which makes a plasmid autonomously replicable, and has a mutation which permits autonomous replication of a plasmid containing the region at a certain temperature, but makes autonomous replication of the plasmid impossible at a temperature higher than that temperature. Further, a plasmid having a temperature sensitive replication control region is referred to as a temperature sensitive plasmid.

The present invention provides a novel temperature sensitive plasmid derived from coryneform bacteria. Because the plasmid can exist together with another conventionally known plasmid in a coryneform bacterial cell, it is useful for breeding of microorganisms harboring such a plasmid and so forth.

DETAILED DESCRIPTION OF THE INVENTION

Figure 1:
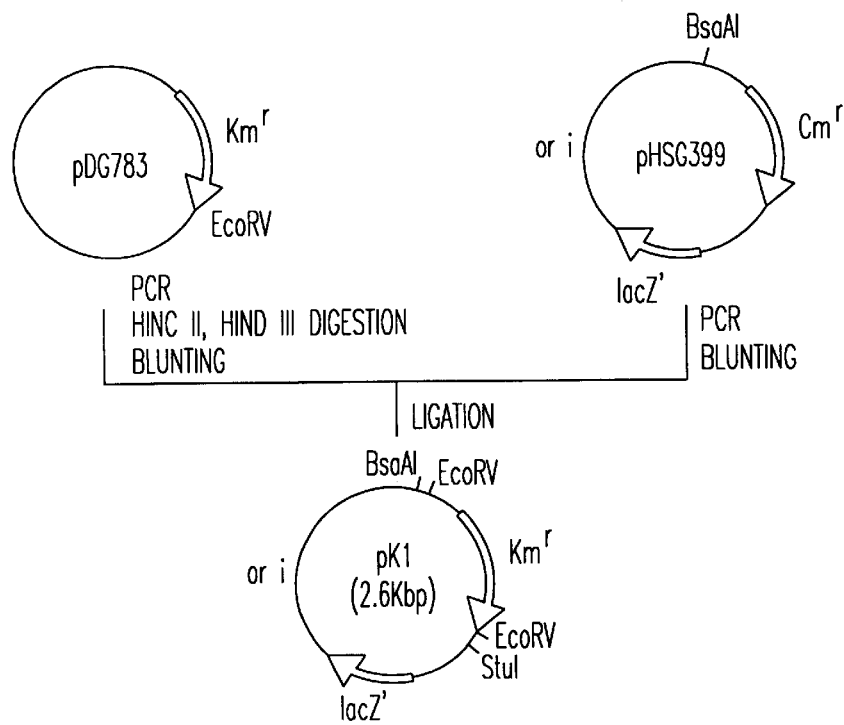
FIG. 1 represents the scheme of construction of the plasmid pK1.

Hereafter, the present invention will be explained in detail.

The plasmid of the present invention has a replication control region exhibiting temperature sensitivity derived from pAM330. pAM330 is a plasmid harbored by a wild-type coryneform bacterium, *Brevibacterium lactofermentum* ATCC13869, and it can be isolated from the strain by a conventional method for isolating plasmids. The ATCC13869 strain can be obtained by any one from the American Type Culture Collection (Address: 10801 University Boulevard, Manassas, Va. 20110-2209, United States of America).

Because pAM330 has a replication control region which differs from conventionally known plasmids derived from coryneform bacteria, for example, pHM1519 [K. Miwa et al., Agric. Biol. Chem., 48, 2901–2903 (1984); Japanese Patent Publication Laid-open (Kokai) No. 58-192900], it does not exhibit incompatibility with these plasmids, and hence it can be used in coryneform bacteria together with these plasmids.

The temperature sensitive replication control region derived from pAM330 can be obtained by subjecting pAM330 or a plasmid derived from pAM330 to a mutagenesis treatment, and selecting a mutant plasmid that is autonomously replicable at a low temperature, but is not autonomously replicable at an elevated temperature within the temperature range in which coryneform bacteria can grow.

Examples of the mutagenesis treatment include in vitro treatment with hydroxylamine etc. (see, for example, G. O. Humpherys et al., *Molec. Gen. Genet.*, 145, 101–108 (1976)), treatments of microorganisms harboring a plasmid with UV irradiation, mutagens used for usual mutagenesis treatments such as N-methyl-N'-nitro-N-nitrosoguanidine (NTG) and nitrous acid and so forth. Among them, the methods utilizing an in vitro treatment are preferred.

By incorporating a marker gene such as an antibiotic resistance gene into a plasmid, the autonomous replication ability of the plasmid subjected to a mutagenesis treatment can be determined based on a phenotype of the marker gene in a coryneform bacterial cell. That is, when a coryneform bacterium cell transformed with such a plasmid that has been subjected to the mutagenesis treatment is cultured in a culture medium added with the corresponding antibiotic at a suitable concentration, for example, if it can grow in the medium, the plasmid is autonomously replicable, and if it cannot grow, the plasmid is not autonomously replicable.

Examples of the marker gene include antibiotic resistance genes derived from bacteria belonging to the genus Streptococcus. Specifically, there can be mentioned a kanamycin resistance gene, tetracycline resistence gene and spectinomycin resistance gene. These genes can be prepared from commercially available vectors, pDG783, pDG1513 and pDG1726 (Anne-Marie Guerout-Fleury et al., *Gene*, 167, 335–337 (1995)). These vectors can be obtained from Bacillus Genetic Stock Center, The Ohio State University, Department of Biochemistry (484 West Twelfth Avenue, Columbus, Ohio 43210, USA).

For example, a kanamycin resistance gene can be obtained by performing polymerase chain reaction [PCR, see White, T. J. et al., *Trends Genet.*, 5, 185 (1989)] using pDG783 as a template and primers having the nucleotide sequences represented as SEQ ID NOS: 1 and 2.

In order to efficiently incorporate a target gene into a chromosome of coryneform bacteria using the plasmid of the present invention, the coryneform bacteria preferably contain, as the marker gene, a drug resistance gene that exhibits sufficient drug resistance even if only one copy of the gene is contained in each cell. The kanamycin resistance gene of *Streptococcus faecalis* exhibits sufficient drug resistance even if only one copy thereof is contained in each cell of coryneform bacteria. Specifically, it can be expected that a coryneform bacterium harboring plasmid of the present invention can grow in a medium that contains at least 25 μg/ml of kanamycin under a suitable condition.

Moreover, the plasmid of the present invention preferably further contains a replication control region that enables autonomous replication of the plasmid in bacteria belonging to the genus Escherichia. If the plasmid of the present invention is made as a shuttle vector by adding a replication control region that functions in *Escherichia coli* as described above, required manipulations such as preparation of plasmid and preparation of recombinant plasmid having a target gene can be performed using *Escherichia coli*. Moreover, a temperature sensitive plasmid can also be obtained by making pAM330 or its derivative into a shuttle vector, and then subjecting it to a mutagenesis treatment.

Examples of the plasmid functioning in *Escherichia coli* include, for example, pUC19, pUC18, pBR322, pHSG299, pHSG298, pHSG399, pHSG398, RSF1010, pMW119, pMW118, pMW219, pMW218 and so forth.

Preparation of plasmid DNA, digestion and ligation of DNA, transformation, PCR, design of oligonucleotides used as primers and the like can be attained by conventional methods well known to those skilled in the art. Such methods are described in Sambrook, J., Fritsch, E. F., and Maniatis, T., "Molecular Cloning: A Laboratory Manual, Second Edition", Cold Spring Harbor Laboratory Press (1989) and so forth.

As specific examples of the plasmid of the present invention, there can be mentioned the temperature sensitive plasmids obtained in the examples mentioned below, p48K, pSFKT1, pSFKT2, pSFKT3, pSFKT4, pSFKT5 and pSFKT6. These plasmids are autonomously replicable at least at 25° C., but are not autonomously replicable at 37° C. in coryneform bacteria.

p48K has the nucleotide sequence of SEQ ID NO: 17 in Sequence Listing containing a wild-type temperature sensitive replication control region that includes a mutation for substitution of T for C at the nucleotide number 1255, mutation for substitution of T for C at the nucleotide number 1534, mutation for substitution of A for G at the nucleotide number 1866, mutation for substitution of A for G at the nucleotide number 2058, mutation for substitution of T for C at the nucleotide number 2187, and mutation for substitution of A for G of at the nucleotide number 3193. Further, pSFKT1, pSFKT2, pSFKT3, pSFKT4, pSFKT5 and pSFKT6 have each of the aforementioned mutations in the mentioned order, respectively. The plasmid of the present invention may have arbitrary 2–5 mutations selected from the aforementioned mutations in combination. The nucleotide sequence represented in SEQ ID NO: 17 contains one open reading frame (ORF). Among the aforementioned mutations, the mutation for substitution of T for C at the nucleotide number 1534 replaces proline at the position of 73 from the N-terminus with serine in the amino acid sequence coded by that ORF (represented in SEQ ID NO: 18). The other nucleotide substitutions do not cause amino acid substitution in the aforementioned amino acid sequence. Those plasmids that contain such a nucleotide sequence that replaces the proline with another amino acid other than serine, and contain a temperature sensitive replication control region that allows autonomous replication of the plasmids at a low temperature but does not allow the autonomous replication at an elevated temperature within the temperature range in which coryneform bacteria can grow are also encompassed within the scope of the plasmid of the present invention.

The temperature sensitive replication control region can be taken out from the plasmid of the present invention, and used to prepare a vector for gene substitution. The replication control region contains regions coding for enzymes involved in the autonomous replication of the plasmid, and a replication origin (ori region), which is recognized by those enzymes so that the replication should be started. The replication control region can be excised by digesting the plasmid with a restriction enzyme that does not recognize these regions, and DNA ligated with the excised DNA can function as a replicon. Thus, derivatives that are constructed from the plasmid of the present invention are also encompassed within the scope of the present invention.

The plasmid of the present invention can be utilized for incorporation of a DNA fragment into a chromosome, gene substitution or gene disruption using homologous recombination. For example, incorporation of a DNA fragment into a chromosome can be performed as follows. A DNA fragment which has a DNA sequence homologous to a DNA sequence present on a chromosome of a coryneform bacterium is ligated to the plasmid of the present invention to construct a recombinant plasmid, and the coryneform bacterium is transformed with the recombinant plasmid. A transformant is cultured at low temperature to cause homologous recombination between the DNA fragment and the DNA sequence having a sequence homologous to the DNA fragment and present on the chromosome of the coryneform bacterium, and a bacterium in which the DNA fragment has been incorporated into the chromosome together with the plasmid is selected.

When a coryneform bacterium obtained as described above is cultured to cause homologous recombination between the DNA fragment incorporated into the chromosome and the DNA sequence originally present on the chromosome, the DNA sequence originally present on the chromosome will be excised from the chromosome with the plasmid. The excised DNA sequence will be deleted from the bacterial cell, when the coryneform bacterium is cultured at an elevated temperature. In this way, the DNA sequence on the chromosome can be replaced with the introduced DNA fragment.

In the present invention, the terms "low temperature" and "elevated temperature" have relative concepts, and the border between them is not particularly limited so long as it is within the temperature range in which coryneform bacteria can grow. Coryneform bacteria can usually grow at 20° C. to 36° C. The border of the low temperature and the elevated temperature is within the range of, for example, 30° C. to 32° C., more specifically about 31° C. The low temperature is preferably 10–27° C., more preferably 20–25° C. The elevated temperature is preferably 31–37° C., more preferably 33–36° C.

To introduce the recombinant DNA prepared as described above to bacterium belonging to the genus Corynebacterium, any known transformation methods can be employed. For instance, employable are a method of treating recipient cells with calcium chloride so as to increase the permeability of DNA, which has been reported for *Escherichia coli* K-12 [see Mandel, M. and Higa, A., *J. Mol. Biol.*, 53, 159 (1970)]; and a method of preparing competent cells from cells which are at the growth phase followed by introducing the DNA thereinto, which has been reported for *Bacillus subtilis* [see Duncan, C. H., Wilson, G. A. and Young, F. E., *Gene*, 1, 153 (1977)]. In addition to these, also employable is a method of making DNA-recipient cells into the protoplast or spheroplast which can easily take up recombinant DNAs followed by introducing the recombinant DNA into the cells, which is known to be applicable to *Bacillus subtilis*, actinomycetes and yeasts [see Chang, S. and Choen, S. N., *Molec. Gen. Genet.*, 168, 111 (1979); Bibb, M. J., Ward, J. M. and Hopwood, O. A., *Nature*, 274, 398 (1978); Hinnen, A., Hicks, J. B. and Fink, G. R., *Proc. Natl. Sci. USA*, 75, 1929 (1978)]. The method of transformation used in embodiments of the present invention is the electric pulse method [refer to Japanese Patent Publication Laid-open (Kokai) No. 2-207791].

The "coryneform bacteria" referred to in the present invention includes bacteria having been hitherto classified into the genus Brevibacterium but united into the genus Corynebacterium at present [*Int. J. Syst. Bacteriol.*, 41, 255 (1981)], and include bacteria belonging to the genus Brevibacterium closely relative to the genus Corynebacterium. Examples of such coryneform L-glutamic acid-producing bacteria include the followings.

*Corynebacterium acetoacidophilum*
*Corynebacterium acetoglutamicum*
*Corynebacterium alkanolyticum*
*Corynebacterium callunae*
*Corynebacterium glutamicum*
*Corynebacterium lilium* (*Corynebacterium glutamicum*)
*Corynebacterium melassecola*
*Corynebacterium thermoaminogenes*
*Corynebacterium herculis*
*Brevibacterium divaricatum* (*Corynebacterium glutamicum*)

*Brevibacterium flavum* (*Corynebacterium glutamicum*)
*Brevibacterium immariophilum*
*Brevibacterium lactofermentum* (*Corynebacterium glutamicum*)
*Brevibacterium roseum*
*Brevibacterium saccharolyticum*
*Brevibacterium thiogenitalis*
*Brevibacterium ammoniagenes* (*Corynebacterium ammoniagenes*)
*Brevibacterium album*
*Brevibacterium cerinum*
*Microbacterium ammoniaphilum*

BEST MODE FOR CARRYING OUT THE INVENTION

Hereafter, the present invention will be further specifically explained with reference to the following examples.

<1> Construction of Vector Containing Drug Resistance Gene of *Streptococcus faecalis*

The kanamycin resistance gene of *Streptococcus faecalis* was amplified by PCR from a known plasmid containing this gene. The nucleotide sequence of the kanamycin resistance gene of *Streptococcus faecalis* has already been clarified [Trieu-Cuot, P. and Courvalin, P., *Gene*, 23(3), 331–341 (1983)]. Based on this sequence, the primers represented in SEQ ID NOS: 1 and 2 were synthesized, and PCR was performed by using pDG783 (Anne-Marie Guerout-Fleury, et al., *Gene*, 167, 335–337 (1995)) as a template to amplify a DNA fragment containing the kanamycin resistance gene and its promoter.

After the aforementioned DNA fragment was purified by using SUPREC02 (Takara Shuzo Co., Ltd.), it was fully digested with restriction enzymes HindIII and HincII, and blunt-ended. The blunt-ending was attained by using Blunting Kit (Takara Shuzo Co., Ltd). This DNA fragment was mixed with and ligated to a DNA fragment obtained by performing PCR using primers shown in SEQ ID NOS: 3 and 4 and pHSG399 [see S. Takeshita, et al., *Gene*, 61, 63–74 (1987)] as a template and blunt-ending the obtained amplification product. The ligation reaction was performed by using DNA Ligation Kit Ver. 2 produced by Takara Shuzo Co., Ltd. Competent cells of *Escherichia coli* JM109 (Takara Shuzo Co., Ltd.) were transformed with the ligated DNA, plated on L medium (10 g/L of Bacto trypton, 5 g/L of Bacto yeast extract, 5 g/L of NaCl, 15 g/L of agar, pH 7.2) containing 10 µg/ml of IPTG (isopropyl-β-D-thiogalactopyranoside), 40 µg/ml of X-Gal (5-bromo-4-chloro-3-indolyl-β-D-galactoside) and 25 µg/ml of kanamycin, and cultured overnight. The appeared blue colonies were picked up, and isolated single colonies to obtain transformant strains.

Plasmids were prepared from the transformant strains by the alkali method (Text for Bioengineering Experiments, Edited by the Society for Bioscience and Bioengineering, Japan, p.105, Baifukan, 1992), and restriction maps were prepared. One having a restriction map equivalent to that of FIG. 1 was designated as pK1. This plasmid is stably retained in *Escherichia coli*, and imparts kanamycin resistance to a host. Moreover, since it contains the lacZ' gene, it is suitably used as a cloning vector.

<2> Construction of Shuttle Vector pSFK6

Figure 2:
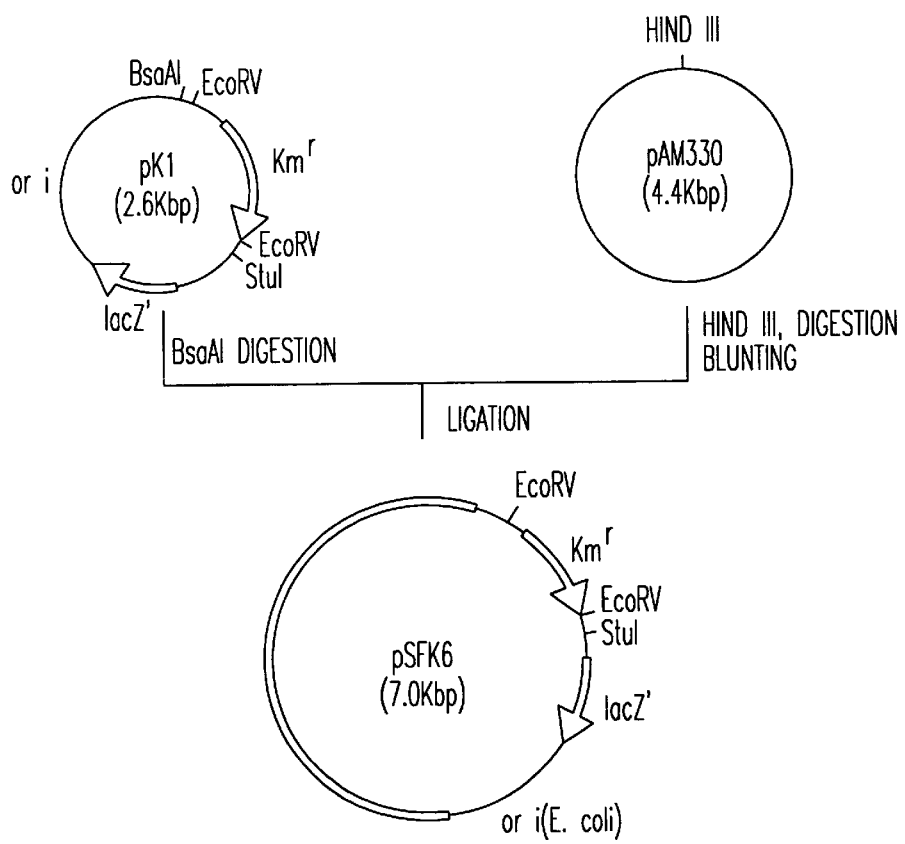
FIG. 2 represents the scheme of construction of the plasmid pSFK6.

As a material for obtaining a temperature sensitive replication control region, a plasmid vector autonomously replicable in both of *Escherichia coli* cells and coryneform bacteria cells was prepared. The plasmid pAM330 extracted from *Brevibacterium lactofermentum* ATCC13869 [see Japanese Patent Publication Laid-open (Kokai) No. 58-67699] was completely digested with a restriction enzyme HindIII, and blunt-ended. This fragment was ligated to a fragment obtained by completely digesting the aforementioned pK1 with a restriction enzyme BsaAI. *Brevibacterium lactofermentum* ATCC13869 was transformed with the ligated DNA. The transformation was performed by the electric pulse method [see Japanese Patent Publication Laid-open (Kokai) No. 2-207791]. Transformants were selected on an M-CM2B plate (10 g/L of polypeptone, 10 g/L of yeast extract, 5 g/L of NaCl, 10 µg/L of biotin, 15 g/L of agar, pH 7.2) containing 25 µg/ml of kanamycin. After cultivation for 2 days, colonies were picked up, and separated into single colonies to obtain the transformants. Plasmid DNAs were prepared from the transformants, and restriction maps were prepared. One having the same restriction map as that of FIG. 2 was designated as pSFK6. This plasmid is autonomously replicable in both of *Escherichia coli* and coryneform bacteria, and imparts kanamycin resistance to a host.

Because the primers shown in SEQ ID NO: 3 and 4 that were used for the construction of pK1 had EcoRV and StuI sites, respectively, only the kanamycin resistance gene can be removed by digesting pSFK6 with EcoRV and StuI. pSFK6 from which the kanamycin resistance gene had been removed was ligated to each of pDG1513 and pDG1726 having tetracycline resistance gene or spectinomycin resistance gene derived from bacteria belonging to the genus Streptococcus (Anne-Marie Guerout-Fleury, et al., *Gene*, 167, 335–337 (1995)), which were digested with BamHI and ClaI, ClaI and EcoRI, and PstI and BamHI, respectively, and blunt-ended, to obtain pSFT6 and pSFS6. Each of these imparts tetracycline resistance or spectinomycin resistance to a host, respectively.

<3> Construction of a Plasmid Having Temperature Sensitive Replication Control Region pSFK6 was treated with hydroxylamine in vitro. The hydroxylamine treatment was performed according to a known method [see, for example, G. O. Humpherys et al., *Molec. Gen. Genet.*, 145, 101–108 (1976)]. DNA undergone the treatment was collected and used for transformation of *Brevibacterium lactofermentum* ATCC13869 strain. The transformants were selected at a low temperature (25° C.) on a CM2B plate containing 25 µg/ml of kanamycin. The appeared transformants were replicated to a similar selection plate, and cultured at an elevated temperature (34° C.). One strain that could not grow on the selection plate containing kanamycin at the elevated temperature was obtained. From this strain, a plasmid was recovered and designated as p48K.

<4> Determination of Nucleotide Sequence of Temperature Sensitive Replication Control Region Nucleotide sequences of replication control region segments in the plasmid pSFK6 having a wild-type replication control region and the plasmid p48K having a temperature sensitive replication control region were determined. The nucleotide sequences were determined on a fully automatic sequencer, ABI310 (ABI), by using DNA Sequencing Kit from ABI. As a result, it was found that there were 6 nucleotide substitutions between the wild-type replication control region and the temperature sensitive replication control region. The nucleotide sequence of the temperature sensitive replication control region segment contained in pSFK6 (full sequence derived from pAM330), which functions in coryneform bacteria, is shown in SEQ ID NO: 17, and the nucleotide sequence of the temperature sensitive replication control region segment contained in p48K, which functions in coryneform bacteria, is shown in SEQ ID NO: 19. Further, the amino acid sequences encoded by ORFs contained in these nucleotide sequences are shown in SEQ ID NOS: 18 and 20. In the temperature sensitive replication control region, the 1255th C is mutated to T, the 1534th C to T, the 1866th G to A, the 2058th G to A, the 2187th C to T and 3193rd G to A. Among these, only the mutation at 1534th position is accompanied by an amino acid mutation, and causes substitution of serine for proline.

<5> Construction of Shuttle Vectors Having Temperature Sensitive Mutation

Figure 3:
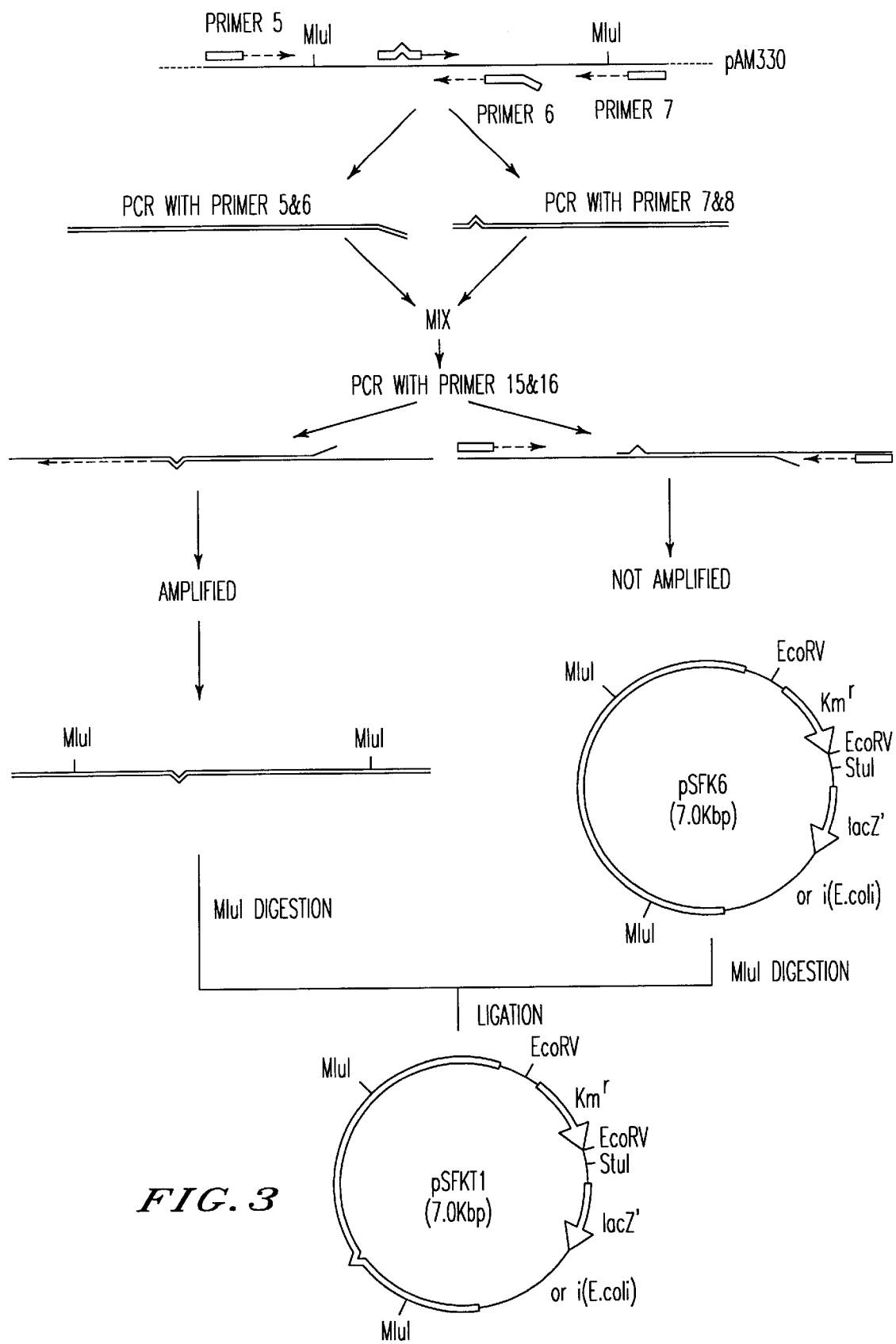
FIG. 3 represents the scheme of construction of the plasmid pSFKT1.

Each one of the six mutations of p48K was introduced into a shuttle vector pSFK6 (see FIG. 3). The introduction of the mutations was performed by a known method [Mikaelian, I., Sergeant, A., Nucleic Acids Res., 20, 376 (1992)]. Specific procedure will be mentioned below. In order to introduce the mutation of 1255th C to T, PCR was performed by using a combination of the primers shown in SEQ ID NOS: 5 and 6, and a combination of the primers shown in SEQ ID NOS: 7 and 8, and pAM330 as a template. Each of the obtained amplification products was purified by subjecting them to agarose gel electrophoresis, and collecting them from the gel. The collection of the DNA fragments from the gel was performed by using EASYTRAP Ver.2 (Takara Shuzo Co., Ltd.). The purified DNAS were mixed in a molar ratio of 1:1, and used as a template for PCR performed by using the primers shown SEQ ID NOS: 15 and 16. The amplification product was fully digested with a restriction enzyme MluI, and subjected to agarose gel electrophoresis to recover a DNA fragment of about 3.2 kb. Similarly, pSFK6 was also completely digested with a restriction enzyme MluI, and subjected to agarose gel electrophoresis to recover a DNA fragment of about 3.8 kb. The obtained DNA fragments were mixed and ligated, and used to transform competent cells of Escherichia coli JM109 (Takara Shuzo Co., Ltd.). The cells were applied on L medium containing 25 µg/ml of kanamycin, and cultured overnight. The appeared colonies were picked up, and isolated single colonies to obtain transformant strains. A plasmid was prepared from the transformant strains by the alkaline method, and the nucleotide sequence of the plasmid was determined to confirm that 1255th C in the sequence shown in SEQ ID NO: 17 was mutated to T. This plasmid was designated as pSFKT1 (FIG. 3). Similarly, plasmids each introduced with one of the other five kinds of mutations, pSFKT2, pSFKT3, pSFKT4, pSFKT5 and pSFKT6, were obtained by using combinations of primers shown in Table 1.

TABLE 1

Primers used for construction of each plasmid

| Introduced mutation | Plasmid | Primers used in first PCR | Primers used in second PCR |
|---|---|---|---|
| $^{1255}$C → T | pSFKT1 | (SEQ ID NO: 5 + SEQ ID NO: 6), (SEQ ID NO: 7 + SEQ ID NO: 8) | SEQ ID NO: 15 + SEQ ID NO: 16 |
| $^{1534}$C → T | pSFKT2 | (SEQ ID NO: 5 + SEQ ID NO: 6), (SEQ ID NO: 7 + SEQ ID NO: 9) | SEQ ID NO: 15 + SEQ ID NO: 16 |
| $^{1866}$G → A | pSFKT3 | (SEQ ID NO: 5 + SEQ ID NO: 6), (SEQ ID NO: 7 + SEQ ID NO: 10) | SEQ ID NO: 15 + SEQ ID NO: 16 |
| $^{2058}$G → A | pSFKT4 | (SEQ ID NO: 5 + SEQ ID NO: 6), (SEQ ID NO: 7 + SEQ ID NO: 11) | SEQ ID NO: 15 + SEQ ID NO: 16 |
| $^{2187}$C → T | pSFKT5 | (SEQ ID NO: 5 + SEQ ID NO: 6), (SEQ ID NO: 7 + SEQ ID NO: 12) | SEQ ID NO: 15 + SEQ ID NO: 16 |
| $^{3193}$G → A | pSFKT6 | (SEQ ID NO: 5 + SEQ ID NO: 13), (SEQ ID NO: 7 + SEQ ID NO: 14) | SEQ ID NO: 15 + SEQ ID NO: 16 |

<6> Confirmation of Temperature Sensitivity of the Shuttle Vector

Brevibacterium lactofermentum ATCC13869 was transformed with pSFKT2, applied to a CM2B plate containing 25 µg/ml of kanamycin, and cultured at 25° C. for two days. The emerged colonies were picked up, separated into single colonies, then inoculated to CM2B broth, and cultured at 25° C. and 34° C. in the absence of kanamycin. Then, plasmid retention ratio after cell division of 15 generations was determined. As a result, as shown in Table 2, it was confirmed that the plasmid was not deleted at 25° C. after cell division of 15 generations, whereas the plasmid was not harbored at 34° C.

TABLE 2

Plasmid retention ratio after cell division of 15 generations

| Culture temperature | Plasmid retention ratio |
|---|---|
| 25° C. | 76% |
| 34° C. | 0.04% or less |

What is claimed is:

1. A plasmid containing a replication control region, wherein the replication control region is obtainable by introducing a mutation into a replication control region of a plasmid pAM330 said mutation allowing the plasmid to replicate autonomously at a low temperature but not allowing the plasmid to replicate autonomously at an elevated temperature in coryneform bacteria within a temperature range in which the bacteria can grow.

2. The plasmid according to claim 1, which further comprises a replication control region that enables autonomous replication of the plasmid in a bacterium belonging to the genus Escherichia.

3. A method for creating a coryneform bacterium in which a DNA fragment is incorporated into its chromosome, which comprises the following steps of:

(a) introducing a recombinant plasmid obtained by ligating a DNA fragment having a sequence homologous to a DNA sequence present on a chromosome of a coryneform bacterium to the plasmid according to claim 2 into a coryneform bacterium cell, (b) culturing the bacterium at a temperature at which the plasmid is autonomously replicable to cause homologous recombination between the DNA fragment and the DNA sequence having a sequence homologous to the DNA fragment present on the chromosome of the coryneform bacterium, and (c) selecting a bacterium in which the DNA fragment is incorporated into the chromosome together with the plasmid.

4. The method according to claim 3, which further comprises the following steps of:

(d) culturing the bacterium to cause homologous recombination between the DNA fragment incorporated into the chromosome and a DNA sequence which has a sequence homologous to the DNA fragment and originally exists on the chromosome of the coryneform bacterium, (e) culturing the bacterium at an elevated temperature to eliminate the DNA sequence which originally exists on the chromosome and the plasmid from the chromosome, and (f) selecting a bacterium in which the DNA sequence on the chromosome is replaced with the DNA fragment.

5. The plasmid according to claim 1, wherein a border between the low temperature and the elevated temperature is present within a range of 30° C. to 32° C.

6. The plasmid according to claim 1, which is autonomously replicable at least at 25° C., but is not autonomously replicable at 37° C. in coryneform bacteria.

7. The plasmid according to claim 1, wherein the replication control region is included in the nucleotide sequence of SEQ ID NO: 17, and contains one or more mutations selected from the group consisting of a mutation for substitution of T for C at the nucleotide number 1255, mutation for substitution of T for C at the nucleotide number 1534, mutation for substitution of A for G at the nucleotide number 1866, mutation for substitution of A for G at the nucleotide number 2058, mutation for substitution of T for C at the nucleotide number 2187, and mutation for substitution of A for G at the nucleotide number 3193 in said nucleotide sequence.

8. The plasmid according to claim 1, wherein the replication control region contains a coding region coding for the amino acid sequence of SEQ ID NO: 18 including a mutation for substitution of an amino acid other than proline for proline at the amino acid number 73.

9. The plasmid according to claim 1, wherein the plasmid contains a marker gene.

10. The plasmid according to claim 9, wherein the marker gene is an antibiotic resistant gene.

11. The plasmid according to claim 10, wherein the antibiotic resistance gene is selected from the geoup consisting of a kanamycin resistance gene, tetracycline resistance gene and spectinomycin resistance gene.

12. A replication control region obtainable by introducing a mutation into a replication control region of the plasmid pAM330, wherein the replication control region is included in the nucleotide sequence of SEQ ID NO: 17, and the mutation is selected from the group consisting of a mutation for substitution of T for C at the nucleotide number 1255, mutation for substitution of T for C at the nucleotide number 1534, mutation for substitution of A for G at the nucleotide number 1866, mutation for substitution of A for G at the nucleotide number 2058, mutation for substitution of T for C at the nucleotide number 2187, and mutation for substitution of A for G at the nucleotide number 3193 in said nucleotide sequence, and the mutation allows a plasmid which contains the replication control region to autonomously replicate at a low temperature but not autonomously replicate at an elevated temperature within a temperature range in which coryneform bacteria can grow.

13. A replication control region obtainable by introducing a mutation into a replication control region of the plasmid pAM330, wherein the replication control region is included in the nucleotide sequence of SEQ ID NO: 17, and the mutation causes, in an amino acid sequence encoded by the nucleotide sequence, a mutation for substitution of an amino acid other than proline for proline at the amino acid number 73 numbered from the N-terminus, and the mutation allows a plasmid which contains the replication control region to autonomously replicate at a low temperature but not autonomously relicate at an elevated temperature within a temperature range in which coryneform bacteria can grow.

* * * * *

SEQUENCE LISTING

<160> NUMBER OF SEQ ID NOS: 20

<210> SEQ ID NO 1
<211> LENGTH: 32
<212> TYPE: DNA
<213> ORGANISM: Artificial Sequence
<220> FEATURE:
<221> NAME/KEY: misc_feature
<223> OTHER INFORMATION: completely synthesized

<400> SEQUENCE: 1
cccgttaact gcttgaaacc caggacaata ac                32

<210> SEQ ID NO 2
<211> LENGTH: 30
<212> TYPE: DNA
<213> ORGANISM: Artificial Sequence
<220> FEATURE:
<221> NAME/KEY: misc_feature
<223> OTHER INFORMATION: completely synthesized

<400> SEQUENCE: 2
cccgttaaca tgtacttcag aaaagattag                   30

<210> SEQ ID NO 3
<211> LENGTH: 26
<212> TYPE: DNA
<213> ORGANISM: Artificial Sequence
<220> FEATURE:
<221> NAME/KEY: misc_feature
<223> OTHER INFORMATION: completely synthesized

<400> SEQUENCE: 3
gatatctacg tgccgatcaa cgtctc                       26

<210> SEQ ID NO 4
<211> LENGTH: 25
<212> TYPE: DNA
<213> ORGANISM: Artificial Sequence
<220> FEATURE:
<221> NAME/KEY: misc_feature
<223> OTHER INFORMATION: completely synthesized

<400> SEQUENCE: 4
aggccttttt ttaaggcagt tattg                        25

<210> SEQ ID NO 5
<211> LENGTH: 30
<212> TYPE: DNA
<213> ORGANISM: Artificial Sequence
<220> FEATURE:
<221> NAME/KEY: misc_feature
<223> OTHER INFORMATION: completely synthesized

<400> SEQUENCE: 5
aaacccgggc tacgtctgat gctttgaatc                   30

<210> SEQ ID NO 6
<211> LENGTH: 27
<212> TYPE: DNA
<213> ORGANISM: Artificial Sequence
<220> FEATURE:
<221> NAME/KEY: misc_feature
<223> OTHER INFORMATION: completely synthesized

<400> SEQUENCE: 6

```
tttgatcccc cgttaacgtc aacaacc                                            27

<210> SEQ ID NO 7
<211> LENGTH: 28
<212> TYPE: DNA
<213> ORGANISM: Artificial Sequence
<220> FEATURE:
<221> NAME/KEY: misc_feature
<223> OTHER INFORMATION: completely synthesized

<400> SEQUENCE: 7
ttttcccggg agcttgccac accccgag                                           28

<210> SEQ ID NO 8
<211> LENGTH: 25
<212> TYPE: DNA
<213> ORGANISM: Artificial Sequence
<220> FEATURE:
<221> NAME/KEY: misc_feature
<223> OTHER INFORMATION: completely synthesized

<400> SEQUENCE: 8
aagacaacgg gcacaacatc cgcac                                              25

<210> SEQ ID NO 9
<211> LENGTH: 24
<212> TYPE: DNA
<213> ORGANISM: Artificial Sequence
<220> FEATURE:
<221> NAME/KEY: misc_feature
<223> OTHER INFORMATION: completely synthesized

<400> SEQUENCE: 9
gggggtcatc tctggctgaa ttgg                                               24

<210> SEQ ID NO 10
<211> LENGTH: 29
<212> TYPE: DNA
<213> ORGANISM: Artificial Sequence
<220> FEATURE:
<221> NAME/KEY: misc_feature
<223> OTHER INFORMATION: completely synthesized

<400> SEQUENCE: 10
gtctgacgat gaactcaagg catttgagg                                          29

<210> SEQ ID NO 11
<211> LENGTH: 24
<212> TYPE: DNA
<213> ORGANISM: Artificial Sequence
<220> FEATURE:
<221> NAME/KEY: misc_feature
<223> OTHER INFORMATION: completely synthesized

<400> SEQUENCE: 11
aaaaccgcgt ctaaagggtc gtac                                               24

<210> SEQ ID NO 12
<211> LENGTH: 22
<212> TYPE: DNA
<213> ORGANISM: Artificial Sequence
<220> FEATURE:
<221> NAME/KEY: misc_feature
<223> OTHER INFORMATION: completely synthesized

<400> SEQUENCE: 12
```

-continued

```
gcgttcgtct tggtcacgtg gg                                              22

<210> SEQ ID NO 13
<211> LENGTH: 23
<212> TYPE: DNA
<213> ORGANISM: Artificial Sequence
<220> FEATURE:
<221> NAME/KEY: misc_feature
<223> OTHER INFORMATION: completely synthesized

<400> SEQUENCE: 13
ttggtgcatc aaacaagatg tag                                             23

<210> SEQ ID NO 14
<211> LENGTH: 27
<212> TYPE: DNA
<213> ORGANISM: Artificial Sequence
<220> FEATURE:
<221> NAME/KEY: misc_feature
<223> OTHER INFORMATION: completely synthesized

<400> SEQUENCE: 14
tgtcctacat cttgtttgat gcaccaa                                         27

<210> SEQ ID NO 15
<211> LENGTH: 24
<212> TYPE: DNA
<213> ORGANISM: Artificial Sequence
<220> FEATURE:
<221> NAME/KEY: misc_feature
<223> OTHER INFORMATION: completely synthesized

<400> SEQUENCE: 15
gaggttttca ccgttctgca tgcc                                            24

<210> SEQ ID NO 16
<211> LENGTH: 23
<212> TYPE: DNA
<213> ORGANISM: Artificial Sequence
<220> FEATURE:
<221> NAME/KEY: misc_feature
<223> OTHER INFORMATION: completely synthesized

<400> SEQUENCE: 16
aactcaccgc cctgcaattc aac                                             23

<210> SEQ ID NO 17
<211> LENGTH: 4447
<212> TYPE: DNA
<213> ORGANISM: Brevibacterium lactofermentum
<220> FEATURE:
<221> NAME/KEY: CDS
<222> LOCATION: (1318)..(2598)

<400> SEQUENCE: 17
aagcttgtct acgtctgatg ctttgaatcg gacggacttg ccgatcttgt atgcggtgat      60
ttttccctcg tttgcccact ttttaatggt ggccggggtg agagctacgc gggcggcgac     120
ctgctgcgct gtgatccaat attcggggtc gttcactggt tcccctttct gatttctggc     180
atagaagaac cccgtgaac tgtgtggttc cggggggttgc tgattttttgc gagacttctc     240 gcgcaattcc ctagcttagg tgaaaacacc atgaaacact agggaaacac ccatgaaaca     300
cccattaggg cagtagggcg gcttcttcgt ctagggcttg catttgggcg gtgatctggt     360
ctttagcgtg tgaaagtgtg tcgtaggtgg cgtgctcaat gcactcgaac gtcacgtcat     420
```

-continued

```
ttaccgggtc acggtgggca aagagaacta gtgggttaga cattgttttc ctcgttgtcg    480
gtggtggtga gcttttctag ccgctcggta aacgcggcga tcatgaactc ttggaggttt    540
tcaccgttct gcatgcctgc gcgcttcatg tcctcacgta gtgccaaagg aacgcgtgcg    600
gtgaccacga cgggcttagc ctttgcctgc gcttctagtg cttcgatggt ggcttgtgcc    660
tgcgcttgct gcgcctgtag tgcctgttga gcttcttgta gttgctgttc tagctgtgcc    720
ttggttgcca tgctttaaga ctctagtagc tttcctgcga tatgtcatgc gcatgcgtag    780
caaacattgt cctgcaactc attcattatg tgcagtgctc ctgttactag tcgtacatac    840
tcatatttac ctagtctgca tgcagtgcat gcacatgcag tcatgtcgtg ctaatgtgta    900
aaacatgtac atgcagattg ctgggggtgc aggggcgga gccacccgt ccatgcgggg     960 tgtgggcctt gccccgccgg tacagacagt gagcaccggg gcacctagtc gcggataccc   1020
cccctaggta tcggacacgt aaccctccca tgtcgatgca aatctttaac attgagtacg   1080
ggtaagctgg cacgcatagc caagctaggc ggccaccaaa caccactaaa aattaatagt   1140
ccctagacaa gacaaacccc cgtgcgagct accaactcat atgcacgggg gcccataaac   1200
ccgaaggggt ttcaattgac aaccatagca ctagctaaga caacgggcac aacacccgca   1260
caaactcgca ctgcgcaacc ccgcacaaca tcgggtctag gtaacactga aatagaa     1317 gtg aac acc tct aag gaa ccg cag gtc aat gag ggt tct aag gtc act    1365
Val Asn Thr Ser Lys Glu Pro Gln Val Asn Glu Gly Ser Lys Val Thr
1               5                   10                  15 cgc gct agg gcg tgg cgt agg caa aac gtc atg tac aag atc acc aat    1413
Arg Ala Arg Ala Trp Arg Arg Gln Asn Val Met Tyr Lys Ile Thr Asn
            20                  25                  30 agt aag gct ctg gcg ggg tgc cat agg tgg cgc agg gac gaa gct gtt    1461
Ser Lys Ala Leu Ala Gly Cys His Arg Trp Arg Arg Asp Glu Ala Val
        35                  40                  45 gcg gtg tcc tgg tcg tct aac ggt gct tcg cag ttt gag ggt ctg caa    1509
Ala Val Ser Trp Ser Ser Asn Gly Ala Ser Gln Phe Glu Gly Leu Gln
    50                  55                  60 aac tct cac tct cgc tgg ggg tca cct ctg gct gaa ttg gaa gtc atg    1557
Asn Ser His Ser Arg Trp Gly Ser Pro Leu Ala Glu Leu Glu Val Met
65                  70                  75                  80 ggc gaa cgc cgc att gag ctg gct att gct act aag aat cac ttg gcg    1605
Gly Glu Arg Arg Ile Glu Leu Ala Ile Ala Thr Lys Asn His Leu Ala
                85                  90                  95 gcg ggt ggc gcg ctc atg atg ttt gtg ggc act gtt cga cac aac cgc    1653
Ala Gly Gly Ala Leu Met Met Phe Val Gly Thr Val Arg His Asn Arg
            100                 105                 110 tca cag tca ttt gcg cag gtt gaa gcg ggt att aag act gcg tac tct    1701
Ser Gln Ser Phe Ala Gln Val Glu Ala Gly Ile Lys Thr Ala Tyr Ser
        115                 120                 125 tcg atg gtg aaa aca tct cag tgg aag aaa gaa cgt gca cgg tac ggg    1749
Ser Met Val Lys Thr Ser Gln Trp Lys Lys Glu Arg Ala Arg Tyr Gly
    130                 135                 140 gtg gag cac acc tat agt gac tat gag gtc aca gac tct tgg gcg aac    1797
Val Glu His Thr Tyr Ser Asp Tyr Glu Val Thr Asp Ser Trp Ala Asn
145                 150                 155                 160 ggt tgg cac ttg cac cgc aac atg ctg ttg ttc ttg gat cgt cca ctg    1845
Gly Trp His Leu His Arg Asn Met Leu Leu Phe Leu Asp Arg Pro Leu
                165                 170                 175 tct gac gat gaa ctc aag gcg ttt gag gat tcc atg ttt tcc cgc tgg    1893
Ser Asp Asp Glu Leu Lys Ala Phe Glu Asp Ser Met Phe Ser Arg Trp
            180                 185                 190 tct gct ggt gtg gtt aag gcc ggt atg gac gcg cca ctg cgt gag cac    1941
```

-continued

| | | |
|---|---|---|
| Ser Ala Gly Val Val Lys Ala Gly Met Asp Ala Pro Leu Arg Glu His<br>          195                    200                  205 | | |
| ggg gtc aaa ctt gat cag gtg tct acc tgg ggt gga gac gct gcg aaa<br>Gly Val Lys Leu Asp Gln Val Ser Thr Trp Gly Gly Asp Ala Ala Lys<br>      210                  215                  220 | 1989 | |
| atg gca acc tac ctc gct aag ggc atg tct cag gaa ctg act ggc tcc<br>Met Ala Thr Tyr Leu Ala Lys Gly Met Ser Gln Glu Leu Thr Gly Ser<br>225                  230                  235                  240 | 2037 | |
| gct act aaa acc gcg tct aag ggg tcg tac acg ccg ttt cag atg ttg<br>Ala Thr Lys Thr Ala Ser Lys Gly Ser Tyr Thr Pro Phe Gln Met Leu<br>                245                  250                  255 | 2085 | |
| gat atg ttg gcc gat caa agc gac gcc ggc gag gat atg gac gct gtt<br>Asp Met Leu Ala Asp Gln Ser Asp Ala Gly Glu Asp Met Asp Ala Val<br>      260                  265                  270 | 2133 | |
| ttg gtg gct cgg tgg cgt gag tat gag gtt ggt tct aaa aac ctg cgt<br>Leu Val Ala Arg Trp Arg Glu Tyr Glu Val Gly Ser Lys Asn Leu Arg<br>275                  280                  285 | 2181 | |
| tcg tcc tgg tca cgt ggg gct aag cgt gct ttg ggc att gat tac ata<br>Ser Ser Trp Ser Arg Gly Ala Lys Arg Ala Leu Gly Ile Asp Tyr Ile<br>          290                  295                  300 | 2229 | |
| gac gct gat gta cgt cgt gaa atg gaa gaa gaa ctg tac aag ctc gcc<br>Asp Ala Asp Val Arg Arg Glu Met Glu Glu Glu Leu Tyr Lys Leu Ala<br>305                  310                  315                  320 | 2277 | |
| ggt ctg gaa gca ccg gaa cgg gtc gaa tca acc cgc gtt gct gtt gct<br>Gly Leu Glu Ala Pro Glu Arg Val Glu Ser Thr Arg Val Ala Val Ala<br>                325                  330                  335 | 2325 | |
| ttg gtg aag ccc gat gat tgg aaa ctg att cag tct gat ttc gcg gtt<br>Leu Val Lys Pro Asp Asp Trp Lys Leu Ile Gln Ser Asp Phe Ala Val<br>      340                  345                  350 | 2373 | |
| agg cag tac gtt cta gat tgc gtg gat aag gct aag gac gtg gcc gct<br>Arg Gln Tyr Val Leu Asp Cys Val Asp Lys Ala Lys Asp Val Ala Ala<br>355                  360                  365 | 2421 | |
| gcg caa cgt gtc gct aat gag gtg ctg gca agt ctg ggt gtg gat tcc<br>Ala Gln Arg Val Ala Asn Glu Val Leu Ala Ser Leu Gly Val Asp Ser<br>      370                  375                  380 | 2469 | |
| acc ccg tgc atg atc gtt atg gat gat gtg gac ttg gac gcg gtt ctg<br>Thr Pro Cys Met Ile Val Met Asp Asp Val Asp Leu Asp Ala Val Leu<br>385                  390                  395                  400 | 2517 | |
| cct act cat ggg gac gct act aag cgt gat ctg aat gcg gcg gtg ttc<br>Pro Thr His Gly Asp Ala Thr Lys Arg Asp Leu Asn Ala Ala Val Phe<br>                405                  410                  415 | 2565 | |
| gcg ggt aat gag cag act att ctt cgc acc cac taaaagcggc ataaccccg<br>Ala Gly Asn Glu Gln Thr Ile Leu Arg Thr His<br>                420                  425 | 2618 | |
| ttcgatattt tgtgcgatga atttatggtc aatgtcgcgg gggcaaacta tgatgggtct | 2678 | |
| tgttgttgac aatggctgat tcatcagga atggaactgt catgctgtta tgtgcctggc | 2738 | |
| tcctaatcaa agctggggac aatgggttgc cccgttgatc tgatctagtt cggattggcg | 2798 | |
| gggcttcact gtatctgggg gtggcatcgt gaatagattg cacaccgtag tgggcagtgt | 2858 | |
| gcacaccata gtgggcatga gtaataccta cgcgcgcgtg ggctagggct taacgcgcgt | 2918 | |
| tttgccgtgc tgcggggcat acgttagcgc atacgctttt ttctgtgaaa ccttttttgtg | 2978 | |
| ttgttgtttc gtgttggttt cctttctgtt ggcggggcaa cttaacgcct gcggggtgg | 3038 | |
| ttgttgacgt taacggggt agttttatt cccctagtgg tttttcagta cgacaatcga | 3098 | |
| gaaagacctg tttcagccag ttcgggtcat gttcgtcggt atggccacgt gcatagcgac | 3158 | |
| cagttttcga gttcactggg attttggtg catcgaacaa gatgtaggac aatgcggttt | 3218 |

```
ctaggtctac tttttgcttt atgccgtaca agccccgtgg gtattcagcg attgattcca     3278
aggcggcttc ccagtcctgt tttgtgaagg actggcttag ttctaggtct gtgtctgggt     3338
agtactgctt gtttgtgtaa gcgccgttgg tgctcattga tgattccttt gaagtgtttg     3398
gagttcggct agtagtgcgg cgtatggtgc tgcttttgc tcgtgatagc tcgccttggc      3458
tatgaggtcg gctaggtagg tttccggggt gcctaggttg cgtaggtcta gcaaatcccg     3518
gtatgtggcc tgtgcgctgc gctggtggtg catacagtcg ttaagctggg cttttacgtc     3578
tgcgatgcgg tggcggttag gcatgttggt gtgcttcttc caagtactca cgggcgggtt     3638
ttgtgtatgc ctggcgtgat gcttctttga gctgttggag ttccgcttgg agtgcgggta     3698
gttcgtccgc gaactgcttg tggtactcgt atttctcttg ttcctgggcg atagcatttg     3758
cgttgaattg cagggcggtg agttcgtcca cgcgtcgttt tgctgcgttg gtcatggtgg     3818
cgtgccattt gcggttgtgg acgcggggtt caaggttgcg cacggctgct cggctaggt      3878 tggtggctgc ttttttcagt gctcgggctt cccgttcctc gtccaacgag agcacctttg     3938
gtttgttggc ttcggctagt ttttgcttct ccgctttgat gagttggtca acttcgtgtt     3998
gggagaggtc gtttttcacg atgcgtcgaa tgtggtcgtt gtgggtgctg agttggtgtg     4058
agaggtagtg gggttctggg atttcggcga gttggtcgag gttggtgtag tgcgggttgc     4118
ggcctggttg gttgggttcg ctggggaggt cgatgtatcc ggttgagtct ccggcgtggt     4178
tgaagtgaat taggcgttgg tagccgtatt cctggttggg gaggtacgac agaatgagga     4238
agtttggtgc ttctcctgca atgagtcgtg cgtgttcgta gttcggtact gggtcgtgct     4298
cggggagaat gttctttgg gtcatggctt ctctttctgt tgctctgtaa gtccgtatgt      4358
gggcatggga aagccccggc aaccctttgg gtcaaccggg gctagatagt cgcttagaat     4418
ggcttctagg ctgcgtctcg ggtgtggc                                        4447
```

<210> SEQ ID NO 18
<211> LENGTH: 427
<212> TYPE: PRT
<213> ORGANISM: Brevibacterium lactofermentum

<400> SEQUENCE: 18

```
Val Asn Thr Ser Lys Glu Pro Gln Val Asn Glu Gly Ser Lys Val Thr
1               5                   10                  15

Arg Ala Arg Ala Trp Arg Arg Gln Asn Val Met Tyr Lys Ile Thr Asn
                20                  25                  30

Ser Lys Ala Leu Ala Gly Cys His Arg Trp Arg Arg Asp Glu Ala Val
            35                  40                  45

Ala Val Ser Trp Ser Ser Asn Gly Ala Ser Gln Phe Glu Gly Leu Gln
        50                  55                  60

Asn Ser His Ser Arg Trp Gly Ser Pro Leu Ala Glu Leu Glu Val Met
65                  70                  75                  80

Gly Glu Arg Arg Ile Glu Leu Ala Ile Ala Thr Lys Asn His Leu Ala
                85                  90                  95

Ala Gly Gly Ala Leu Met Met Phe Gly Thr Val Arg His Asn Arg
            100                 105                 110

Ser Gln Ser Phe Ala Gln Val Glu Ala Gly Ile Lys Thr Ala Tyr Ser
        115                 120                 125

Ser Met Val Lys Thr Ser Gln Trp Lys Lys Glu Arg Ala Arg Tyr Gly
    130                 135                 140

Val Glu His Thr Tyr Ser Asp Tyr Glu Val Thr Asp Ser Trp Ala Asn
145                 150                 155                 160
```

```
Gly Trp His Leu His Arg Asn Met Leu Leu Phe Leu Asp Arg Pro Leu
                165                 170                 175
Ser Asp Asp Glu Leu Lys Ala Phe Glu Asp Ser Met Phe Ser Arg Trp
            180                 185                 190
Ser Ala Gly Val Val Lys Ala Gly Met Asp Ala Pro Leu Arg Glu His
        195                 200                 205
Gly Val Lys Leu Asp Gln Val Ser Thr Trp Gly Gly Asp Ala Ala Lys
    210                 215                 220
Met Ala Thr Tyr Leu Ala Lys Gly Met Ser Gln Glu Leu Thr Gly Ser
225                 230                 235                 240
Ala Thr Lys Thr Ala Ser Lys Gly Ser Tyr Thr Pro Phe Gln Met Leu
                245                 250                 255
Asp Met Leu Ala Asp Gln Ser Asp Ala Gly Glu Asp Met Asp Ala Val
            260                 265                 270
Leu Val Ala Arg Trp Arg Glu Tyr Glu Val Gly Ser Lys Asn Leu Arg
        275                 280                 285
Ser Ser Trp Ser Arg Gly Ala Lys Arg Ala Leu Gly Ile Asp Tyr Ile
    290                 295                 300
Asp Ala Asp Val Arg Arg Glu Met Glu Glu Leu Tyr Lys Leu Ala
305                 310                 315                 320
Gly Leu Glu Ala Pro Glu Arg Val Glu Ser Thr Arg Val Ala Val Ala
                325                 330                 335
Leu Val Lys Pro Asp Asp Trp Lys Leu Ile Gln Ser Asp Phe Ala Val
            340                 345                 350
Arg Gln Tyr Val Leu Asp Cys Val Asp Lys Ala Lys Asp Val Ala Ala
        355                 360                 365
Ala Gln Arg Val Ala Asn Glu Val Leu Ala Ser Leu Gly Val Asp Ser
    370                 375                 380
Thr Pro Cys Met Ile Val Met Asp Asp Val Asp Leu Asp Ala Val Leu
385                 390                 395                 400
Pro Thr His Gly Asp Ala Thr Lys Arg Asp Leu Asn Ala Ala Val Phe
                405                 410                 415
Ala Gly Asn Glu Gln Thr Ile Leu Arg Thr His
            420                 425

<210> SEQ ID NO 19
<211> LENGTH: 4447
<212> TYPE: DNA
<213> ORGANISM: Brevibacterium lactofermentum
<220> FEATURE:
<221> NAME/KEY: CDS
<222> LOCATION: (1318)..(2598)

<400> SEQUENCE: 19
aagcttgtct acgtctgatg ctttgaatcg gacggacttg ccgatcttgt atgcggtgat      60
ttttccctcg tttgcccact ttttaatggt ggccggggtg agagctacgc gggcggcgac     120
ctgctgcgct gtgatccaat attcggggtc gttcactggt tcccctttct gatttctggc     180
atagaagaac ccccgtgaac tgtgtggttc cgggggttgc tgattttttgc gagacttctc    240
gcgcaattcc ctagcttagg tgaaaacacc atgaaacact agggaaacac ccatgaaaca     300
cccattaggg cagtagggcg gcttcttcgt ctagggcttg catttgggcg gtgatctggt     360
cttttagcgtg tgaaagtgtg tcgtaggtgg cgtgctcaat gcactcgaac gtcacgtcat    420
ttaccgggtc acggtgggca aagagaacta gtgggttaga cattgttttc ctcgttgtcg    480
```

-continued

```
gtggtggtga gcttttctag ccgctcggta aacgcggcga tcatgaactc ttggaggttt    540
tcaccgttct gcatgcctgc gcgcttcatg tcctcacgta gtgccaaagg aacgcgtgcg    600
gtgaccacga cgggcttagc ctttgcctgc gcttctagtg cttcgatggt ggcttgtgcc    660
tgcgcttgct gcgcctgtag tgcctgttga gcttcttgta gttgctgttc tagctgtgcc    720
ttggttgcca tgctttaaga ctctagtagc tttcctgcga tatgtcatgc gcatgcgtag    780
caaacattgt cctgcaactc attcattatg tgcagtgctc ctgttactag tcgtacatac    840
tcatatttac ctagtctgca tgcagtgcat gcacatgcag tcatgtcgtg ctaatgtgta    900
aaacatgtac atgcagattg ctgggggtgc aggggcgga gccaccctgt ccatgcgggg     960
tgtggggctt gccccgccgg tacagacagt gagcaccggg gcacctagtc gcggataccc   1020
cccctaggta tcggacacgt aaccctccca tgtcgatgca aatctttaac attgagtacg   1080
ggtaagctgg cacgcatagc caagctaggc ggccaccaaa caccactaaa aattaatagt   1140
tcctagacaa gacaaacccc cgtgcgagct accaactcat atgcacgggg gccacataac   1200
ccgaaggggt ttcaattgac aaccatagca ctagctaaga caacgggcac aacatccgca   1260
caaactcgca ctgcgcaacc ccgcacaaca tcgggtctag gtaacactga aatagaa      1317 gtg aac acc tct aag gaa ccg cag gtc aat gag ggt tct aag gtc act    1365
Val Asn Thr Ser Lys Glu Pro Gln Val Asn Glu Gly Ser Lys Val Thr
1               5                   10                  15 cgc gct agg gcg tgg cgt agg caa aac gtc atg tac aag atc acc aat    1413
Arg Ala Arg Ala Trp Arg Arg Gln Asn Val Met Tyr Lys Ile Thr Asn
            20                  25                  30 agt aag gct ctg gcg ggg tgc cat agg tgg cgc agg gac gaa gct gtt    1461
Ser Lys Ala Leu Ala Gly Cys His Arg Trp Arg Arg Asp Glu Ala Val
        35                  40                  45 gcg gtg tcc tgg tcg tct aac ggt gct tcg cag ttt gag ggt ctg caa    1509
Ala Val Ser Trp Ser Ser Asn Gly Ala Ser Gln Phe Glu Gly Leu Gln
    50                  55                  60 aac tct cac tct cgc tgg ggg tca tct ctg gct gaa ttg gaa gtc atg    1557
Asn Ser His Ser Arg Trp Gly Ser Ser Leu Ala Glu Leu Glu Val Met
65                  70                  75                  80 ggc gaa cgc cgc att gag ctg gct att gct act aag aat cac ttg gcg    1605
Gly Glu Arg Arg Ile Glu Leu Ala Ile Ala Thr Lys Asn His Leu Ala
                85                  90                  95 gcg ggt ggc gcg ctc atg atg ttt gtg ggc act gtt cga cac aac cgc    1653
Ala Gly Gly Ala Leu Met Met Phe Val Gly Thr Val Arg His Asn Arg
            100                 105                 110 tca cag tca ttt gcg cag gtt gaa gcg ggt att aag act gcg tac tct    1701
Ser Gln Ser Phe Ala Gln Val Glu Ala Gly Ile Lys Thr Ala Tyr Ser
        115                 120                 125 tcg atg gtg aaa aca tct cag tgg aag aaa gaa cgt gca cgg tac ggg    1749
Ser Met Val Lys Thr Ser Gln Trp Lys Lys Glu Arg Ala Arg Tyr Gly
    130                 135                 140 gtg gag cac acc tat agt gac tat gag gtc aca gac tct tgg gcg aac    1797
Val Glu His Thr Tyr Ser Asp Tyr Glu Val Thr Asp Ser Trp Ala Asn
145                 150                 155                 160 ggt tgg cac ttg cac cgc aac atg ctg ttg ttc ttg gat cgt cca ctg    1845
Gly Trp His Leu His Arg Asn Met Leu Leu Phe Leu Asp Arg Pro Leu
                165                 170                 175 tct gac gat gaa ctc aag gca ttt gag gat tcc atg ttt tcc cgc tgg    1893
Ser Asp Asp Glu Leu Lys Ala Phe Glu Asp Ser Met Phe Ser Arg Trp
            180                 185                 190 tct gct ggt gtg gtt aag gcc ggt atg gac gcg cca ctg cgt gag cac    1941
Ser Ala Gly Val Val Lys Ala Gly Met Asp Ala Pro Leu Arg Glu His
        195                 200                 205
```

-continued

```
ggg gtc aaa ctt gat cag gtg tct acc tgg ggt gga gac gct gcg aaa         1989
Gly Val Lys Leu Asp Gln Val Ser Thr Trp Gly Gly Asp Ala Ala Lys
        210                 215                 220 atg gca acc tac ctc gct aag ggc atg tct cag gaa ctg act ggc tcc         2037
Met Ala Thr Tyr Leu Ala Lys Gly Met Ser Gln Glu Leu Thr Gly Ser
225                 230                 235                 240 gct act aaa acc gcg tct aaa ggg tcg tac acg ccg ttt cag atg ttg         2085
Ala Thr Lys Thr Ala Ser Lys Gly Ser Tyr Thr Pro Phe Gln Met Leu
                245                 250                 255 gat atg ttg gcc gat caa agc gac gcc ggc gag gat atg gac gct gtt         2133
Asp Met Leu Ala Asp Gln Ser Asp Ala Gly Glu Asp Met Asp Ala Val
            260                 265                 270 ttg gtg gct cgg tgg cgt gag tat gag gtt ggt tct aaa aac ctg cgt         2181
Leu Val Ala Arg Trp Arg Glu Tyr Glu Val Gly Ser Lys Asn Leu Arg
        275                 280                 285 tcg tct tgg tca cgt ggg gct aag cgt gct ttg ggc att gat tac ata         2229
Ser Ser Trp Ser Arg Gly Ala Lys Arg Ala Leu Gly Ile Asp Tyr Ile
290                 295                 300 gac gct gat gta cgt cgt gaa atg gaa gaa gaa ctg tac aag ctc gcc         2277
Asp Ala Asp Val Arg Arg Glu Met Glu Glu Glu Leu Tyr Lys Leu Ala
305                 310                 315                 320 ggt ctg gaa gca ccg gaa cgg gtc gaa tca acc cgc gtt gct gtt gct         2325
Gly Leu Glu Ala Pro Glu Arg Val Glu Ser Thr Arg Val Ala Val Ala
                325                 330                 335 ttg gtg aag ccc gat gat tgg aaa ctg att cag tct gat ttc gcg gtt         2373
Leu Val Lys Pro Asp Asp Trp Lys Leu Ile Gln Ser Asp Phe Ala Val
            340                 345                 350 agg cag tac gtt cta gat tgc gtg gat aag gct aag gac gtg gcc gct         2421
Arg Gln Tyr Val Leu Asp Cys Val Asp Lys Ala Lys Asp Val Ala Ala
        355                 360                 365 gcg caa cgt gtc gct aat gag gtg ctg gca agt ctg ggt gtg gat tcc         2469
Ala Gln Arg Val Ala Asn Glu Val Leu Ala Ser Leu Gly Val Asp Ser
370                 375                 380 acc ccg tgc atg atc gtt atg gat gat gtg gac ttg gac gcg gtt ctg         2517
Thr Pro Cys Met Ile Val Met Asp Asp Val Asp Leu Asp Ala Val Leu
385                 390                 395                 400 cct act cat ggg gac gct act aag cgt gat ctg aat gcg gcg gtg ttc         2565
Pro Thr His Gly Asp Ala Thr Lys Arg Asp Leu Asn Ala Ala Val Phe
                405                 410                 415 gcg ggt aat gag cag act att ctt cgc acc cac taaaagcggc ataaaccccg       2618
Ala Gly Asn Glu Gln Thr Ile Leu Arg Thr His
            420                 425 ttcgatattt tgtgcgatga atttatggtc aatgtcgcgg gggcaaacta tgatgggtct       2678
tgttgttgac aatggctgat ttcatcagga atggaactgt catgctgtta tgtgcctggc       2738
tcctaatcaa agctggggac aatgggttgc cccgttgatc tgatctagtt cggattggcg       2798
gggcttcact gtatctgggg gtggcatcgt gaatagattg cacaccgtag tgggcagtgt       2858
gcacaccata gtgggcatga gtaataccta cgcgcgcgtg ggctagggct taacgcgcgt       2918
tttgccgtgc tgcggggcat acgttagcgc atacgctttt ttctgtgaaa ccttttttgtg      2978 ttgttgtttc gtgttggttt cctttctgtt ggcggggcaa cttaacgcct gcggggggtgg     3038 ttgttgacgt taacgggggt agtttttatt ccccctagtgg ttttttcagta cgacaatcga    3098 gaaagacctg tttcagccag ttcgggtcat gttcgtcggt atggccacgt gcatagcgac      3158
cagttttcga gttcactggg atttttggtg catcaaacaa gatgtaggac aatgcggttt      3218
ctaggtctac ttttttgcttt atgccgtaca agcccccgtgg gtattcagcg attgattcca   3278
```

-continued

```
aggcggcttc ccagtcctgt tttgtgaagg actggcttag ttctaggtct gtgtctgggt    3338
agtactgctt gtttgtgtaa gcgccgttgg tgctcattga tgattccttt gaagtgtttg    3398
gagttcggct agtagtgcgg cgtatggtgc tgcttttttgc tcgtgatagc tcgccttggc    3458
tatgaggtcg gctaggtagg tttccggggt gcctaggttg cgtaggtcta gcaaatcccg    3518
gtatgtggcc tgtgcgctgc gctggtggtg catacagtcg ttaagctggg cttttacgtc    3578
tgcgatgcgg tggcggttag gcatgttggt gtgcttcttc caagtactca cgggcgggtt    3638
ttgtgtatgc ctggcgtgat gcttctttga gctgttggag ttccgcttgg agtgcgggta    3698
gttcgtccgc gaactgcttg tggtactcgt atttctcttg ttcctgggcg atagcatttg    3758
cgttgaattg cagggcggtg agttcgtcca cgcgtcgttt tgctgcgttg gtcatggtgg    3818
cgtgccattt gcggttgtgg acgcggggtt caaggttgcg cacggctgct tcggctaggt    3878
tggtggctgc tttttttcagt gctcgggctt cccgttcctc gtccaacgag agcacctttg    3938
gtttgttggc ttcggctagt ttttgcttct ccgctttgat gagttggtca acttcgtgtt    3998
gggagaggtc gtttttcacg atgcgtcgaa tgtggtcgtt gtgggtgctg agttggtgtg    4058
agaggtagtg gggttctggg atttcggcga gttggtcgag gttggtgtag tgcgggttgc    4118
ggcctggttg gttgggttcg ctggggaggt cgatgtatcc ggttgagtct ccggcgtggt    4178
tgaagtgaat taggcgttgg tagccgtatt cctggttggg gaggtacgac agaatgagga    4238
agtttggtgc ttctcctgca atgagtcgtg cgtgttcgta gttcggtact gggtcgtgct    4298
cggggagaat gttcttttgg gtcatggctt ctctttctgt tgctctgtaa gtccgtatgt    4358
gggcatggga aagccccggc aacccctttgg gtcaaccggg gctagatagt cgcttagaat    4418
ggcttctagg ctgcgtctcg gggtgtggc                                      4447
```

<210> SEQ ID NO 20
<211> LENGTH: 427
<212> TYPE: PRT
<213> ORGANISM: Brevibacterium lactofermentum

<400> SEQUENCE: 20

```
Val Asn Thr Ser Lys Glu Pro Gln Val Asn Glu Gly Ser Lys Val Thr
1               5                   10                  15

Arg Ala Arg Ala Trp Arg Arg Gln Asn Val Met Tyr Lys Ile Thr Asn
            20                  25                  30

Ser Lys Ala Leu Ala Gly Cys His Arg Trp Arg Arg Asp Glu Ala Val
        35                  40                  45

Ala Val Ser Trp Ser Ser Asn Gly Ala Ser Gln Phe Glu Gly Leu Gln
    50                  55                  60

Asn Ser His Ser Arg Trp Gly Ser Ser Leu Ala Glu Leu Glu Val Met
65                  70                  75                  80

Gly Glu Arg Arg Ile Glu Leu Ala Ile Ala Thr Lys Asn His Leu Ala
                85                  90                  95

Ala Gly Gly Ala Leu Met Met Phe Val Gly Thr Val Arg His Asn Arg
            100                 105                 110

Ser Gln Ser Phe Ala Gln Val Glu Ala Gly Ile Lys Thr Ala Tyr Ser
        115                 120                 125

Ser Met Val Lys Thr Ser Gln Trp Lys Lys Glu Arg Ala Arg Tyr Gly
    130                 135                 140

Val Glu His Thr Tyr Ser Asp Tyr Glu Val Thr Asp Ser Trp Ala Asn
145                 150                 155                 160

Gly Trp His Leu His Arg Asn Met Leu Leu Phe Leu Asp Arg Pro Leu
```

```
                              165                     170                     175
Ser Asp Asp Glu Leu Lys Ala Phe Glu Asp Ser Met Phe Ser Arg Trp
            180                     185                 190

Ser Ala Gly Val Val Lys Ala Gly Met Asp Ala Pro Leu Arg Glu His
            195                     200                 205

Gly Val Lys Leu Asp Gln Val Ser Thr Trp Gly Gly Asp Ala Ala Lys
        210                     215                 220

Met Ala Thr Tyr Leu Ala Lys Gly Met Ser Gln Glu Leu Thr Gly Ser
225                     230                     235                     240

Ala Thr Lys Thr Ala Ser Lys Gly Ser Tyr Thr Pro Phe Gln Met Leu
                245                     250                 255

Asp Met Leu Ala Asp Gln Ser Asp Ala Gly Glu Asp Met Asp Ala Val
                260                     265                 270

Leu Val Ala Arg Trp Arg Glu Tyr Glu Val Gly Ser Lys Asn Leu Arg
            275                     280                 285

Ser Ser Trp Ser Arg Gly Ala Lys Arg Ala Leu Gly Ile Asp Tyr Ile
        290                     295                 300

Asp Ala Asp Val Arg Arg Glu Met Glu Glu Glu Leu Tyr Lys Leu Ala
305                     310                     315                     320

Gly Leu Glu Ala Pro Glu Arg Val Glu Ser Thr Arg Val Ala Val Ala
                325                     330                 335

Leu Val Lys Pro Asp Asp Trp Lys Leu Ile Gln Ser Asp Phe Ala Val
                340                     345                 350

Arg Gln Tyr Val Leu Asp Cys Val Asp Lys Ala Lys Asp Val Ala Ala
        355                     360                 365

Ala Gln Arg Val Ala Asn Glu Val Leu Ala Ser Leu Gly Val Asp Ser
    370                     375                 380

Thr Pro Cys Met Ile Val Met Asp Asp Val Asp Leu Asp Ala Val Leu
385                     390                     395                     400

Pro Thr His Gly Asp Ala Thr Lys Arg Asp Leu Asn Ala Ala Val Phe
                405                     410                 415

Ala Gly Asn Glu Gln Thr Ile Leu Arg Thr His
            420                     425
```